United States Patent [19]

Spencer

[11] Patent Number: 5,003,830
[45] Date of Patent: Apr. 2, 1991

[54] SAMPLE EXTRACTION SYSTEM

[76] Inventor: R. Wilson Spencer, P.O. Box 22586, Houston, Tex. 77227

[21] Appl. No.: 435,935

[22] Filed: Nov. 13, 1989

Related U.S. Application Data

[63] Continuation-in-part of Ser. No. 304,815, Jan. 31, 1989, abandoned, which is a continuation of Ser. No. 55,720, May 29, 1987, Pat. No. 4,800,761.

[51] Int. Cl.⁵ .............................................. G01N 1/14
[52] U.S. Cl. .................................................. 73/863.83
[58] Field of Search ........... 73/863.61, 863.71, 863.72, 73/863.81–863.86, 864.34

[56] References Cited

U.S. PATENT DOCUMENTS

| | | | |
|---|---|---|---|
| 1,669,776 | 5/1928 | Osburn | 73/863.82 |
| 1,739,731 | 12/1929 | Osborne | 73/863.83 |
| 2,475,857 | 7/1949 | Reinert | 73/422 |
| 3,282,113 | 11/1966 | Sachnik | 73/422 |
| 3,681,997 | 8/1972 | Allen et al. | 73/422 TC |
| 3,950,135 | 1/1976 | Bellinga | 73/422 |
| 3,974,697 | 8/1976 | Speth | 73/422 |
| 4,037,475 | 7/1977 | Topham | 73/422 |
| 4,118,987 | 10/1978 | Zeh | 73/422 |
| 4,134,239 | 1/1979 | Bohl et al. | 72/23 |
| 4,207,450 | 6/1980 | Mittleman | 250/343 |
| 4,268,268 | 5/1981 | Blum | 23/250 |
| 4,272,247 | 6/1981 | Strain et al. | 23/230 |
| 4,307,620 | 12/1981 | Jiskoot | 73/863.83 |
| 4,562,747 | 1/1986 | Jaeger | 73/863.54 |
| 4,616,515 | 10/1986 | Dancoine | 73/863.83 |
| 4,712,434 | 12/1987 | Herwig et al. | 73/863.71 |
| 4,800,761 | 1/1989 | Spencer | 73/863.71 |
| 4,831,887 | 5/1989 | Crossley | 73/864.34 |

FOREIGN PATENT DOCUMENTS 0086749 4/1959 Denmark .......................... 73/863.61

*Primary Examiner*—Robert Raevis
*Attorney, Agent, or Firm*—Robert C. Tucker; William D. Kiesel

[57] ABSTRACT

In combination with a wheeled transport tank or marine transport tank, such as a railroad tank car, highway tank trailer, or marine barge having a reservoir, a sample extraction system, comprising a suction line extending into the reservoir; a pump having a suction port and a discharge port, the suction port being connected to the suction line; a discharge line having a first end and a second end, connected at the first end to the discharge port; a sampling unit, for removing a sample from the discharge line, having an inlet and an outlet, the inlet being connected to the second end of the discharge line; a return line, connected on one end to the outlet of the sampling unit and terminating within the reservoir.

8 Claims, 5 Drawing Sheets

SAMPLE EXTRACTION SYSTEM

BACKGROUND OF THE INVENTION

1. Related Applications

This is a continuation-in-part application of U.S. patent application, Ser. No. 304,815, filed on Jan. 31, 1989, now abandoned, which is a continuation of U.S. patent application, Ser. No. 55,720, now U.S. Pat. No. 4,800,761, filed on May 29, 1987, by the inventor herein, entitled "Sample Extraction System", specific mention being made to obtain the benefit of the parent applications' filing date.

2. Field of the Invention

This invention relates generally to devices for sampling flowing fluids and, more particularly, to such devices which operate within a closed loop system.

3. Prior Art

In industrial chemical plants, as well as other industrial process operations, it is often necessary to obtain samples of fluids flowing in pipelines or various other types of vessels. Often, such fluids are of a hazardous nature, requiring that exposure of personnel to the sample be minimized or eliminated. In most applications when a sample is taken from a line flowing under pressure, samples are taken in sample cylinders. Such cylinders are well-known in the art. A typical cylinder is usually provided with a valve on either end, allowing a sample to be encased therein.

Various methods have been attempted in the art to safely force the sample into the cylinder. One method is to simply connect one valve at the connected end and bleed the other end of the cylinder using the opposite valve until the cylinder is full of sample and entrained gases are displaced. This method obviously has its limitations with hazardous materials, since the bleeding step offers the possibility of exposing sampling personnel to the sample (a clear violation of current federal regulations). Other methods create a vacuum in the cylinder; elaborate means such as mercury or water displacement are also used. All of the prior art methods are prone to failure as well as exposure of sampling personnel to the sample. Further, these methods do not always result in a representative sample being contained in the cylinder or the sample container.

Stringent environmental regulations have resulted from an increasing concern for the safety of sampling personnel as well as exposure or discharge of hazardous materials to the atmosphere. Regulatory and safety concerns have thus severely limited sampling, resulting in elaborate and expensive containment schemes. Nevertheless, monitoring of industrial processes must still take place. Highway tank trailers, railroad cars or marine transport tanks, such as tankers or barges carrying hazardous materials such as liquified petroleum gases, ammonia ethylene oxide or other liquids or gasses under pressure are still sampled by an operator filling a sample cylinder by any one of several means known in the art, and previously mentioned in this application. These methods expose the operator to the fluid being sampled or require the taking of elaborate safety precautions and wearing bulky and often cumbersome safety equipment. The prior art devices have not managed to economically provide the necessary safety while maintaining the integrity of the sample and demonstrate the need for the present invention.

SUMMARY OF THE INVENTION

Therefore, it is an object of this invention to provide a sample extraction system which minimizes exposure of sampling personnel to the sample.

It is another object of this invention to provide a sample extraction system which will economically obtain a representative sample and maintain maximum safety.

It is still another object of this invention to provide a sample extraction system which will not utilize significant external power to take a sample.

It is still another object of this invention to provide a sample extraction system which will return excess sample and entrained gases back into the source from which the sample came.

It is another object of this invention to provide a sample extraction system which will operate in combination with a wheeled transport tank or a marine transport tank, providing a means for readily sampling the contents of the tank.

It is yet a further object of this invention to provide a sample extraction system which will accomplish all of the above objectives.

Accordingly, a sample extraction system is provided, comprising a block fitting including an inlet, an outlet, an interior passageway providing communication between the inlet and the outlet, thereby allowing flow through the block fitting, a venturi section positioned in the interior passageway, a sample port, a sample passageway connecting the interior passageway and the sample port between the inlet and the venturi section, a reentry port, and a reentry passageway connecting the reentry port and the venturi section; a loop entry line, connected on one end to a main flow line, and on the other end to the inlet of the block fitting; a loop exit line connected on one end to the main flow line, and on the other end to the outlet of the block fitting; a sample container, having an inlet and an outlet; a sample inlet line, connected on one end to the inlet of the sample container; at least one sample inlet valve, positioned in the sample inlet line; a sample exit line, connected on one end to the outlet of the sample container, and on the other end to the reentry port; and at least one sample exit valve, positioned in the sample exit line.

When equipped with a circulating system and combined with a wheeled transport tank such as a railroad tank car or highway tank trailer or marine transport tank having a reservoir, the invention enables the user to accomplish representative emission-free sampling of such transport containers and comprises a suction line extending into the reservoir; a pump having a suction port and a discharge port, the suction port being connected to the suction line; a discharge line having a first end and a second end, connected at the first end to the discharge port; a sampling unit, for removing a sample from the discharge line, having an inlet and an outlet, the inlet being connected to the second end of the discharge line; a return line, connected on one end to the outlet of the sampling unit and terminating within the reservoir.

DETAILED DESCRIPTION OF PREFERRED EMBODIMENTS OF THE INVENTION

Figure 1:
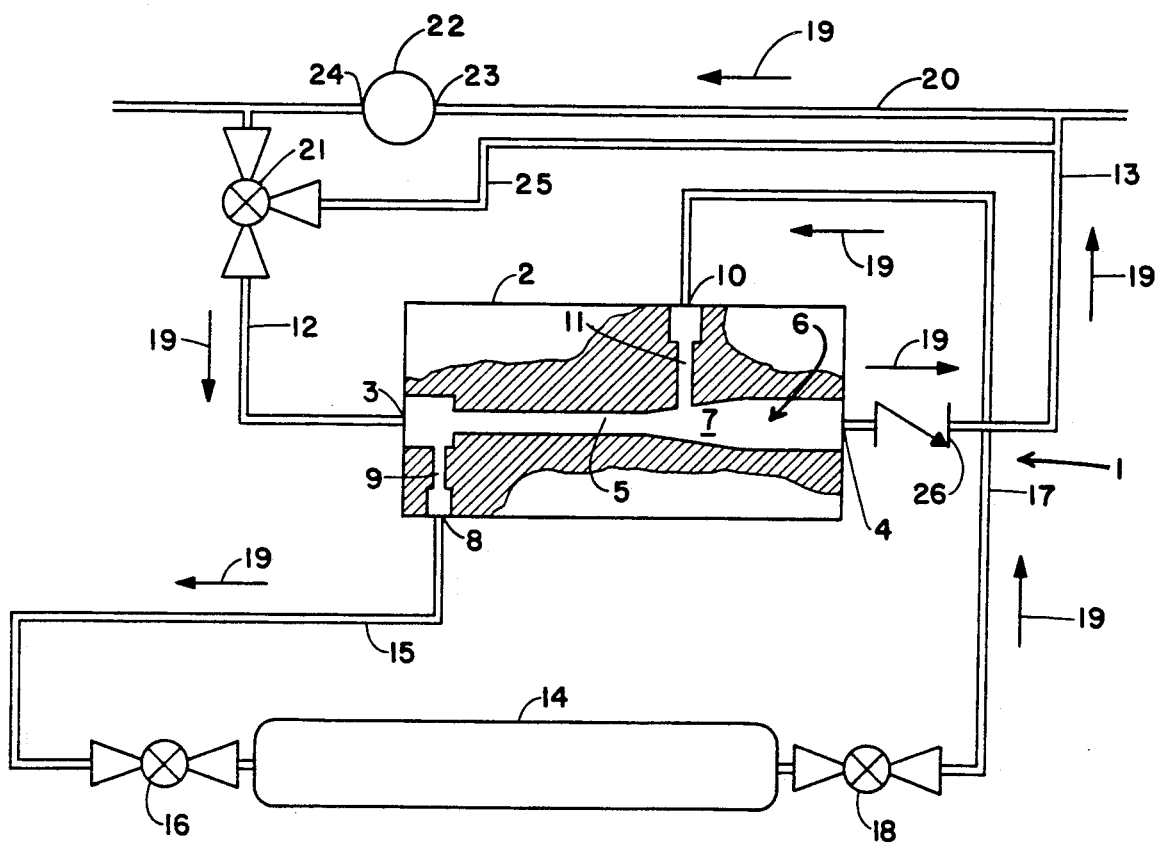
FIG. 1 is a side view of the invention with portions of the block fitting of the invention removed to sectionally reveal the interior components of the fitting.

The sample extraction system 1 is shown in FIG. 1 connected to a main flow line 20, from which a sample of flowing fluid is extracted utilizing the system 1. The system 1 utilizes the pressure differential in main flow line 20 to inject a sample of the flowing fluid into a sample container 14, usually a sample cylinder. Pressure differential may be created in a number of ways. Typically the invention may be attached to main flow line 20 on either side of an existing pressure differential caused by devices such as a pump 22 having suction port 23 and discharge port 24. Pressure differential may also be induced by devices such as an orifice plate (not shown).

As shown, the sample will flow from main flow line 20 on the discharge side of pump 22 through loop entry line 12 and into block fitting 2 at block fitting inlet 3. Flow (shown by arrows 19) is directed through block fitting interior passageway 5, exiting outlet 4 and reentering main flow line 20 through loop exit line 13, which is connected to main flow line 20 on the suction side of pump 22. Thus, a constant flow is established through block fitting 2. When sample loop valve 21 is utilized in the three-way embodiment shown, flow may be diverted through by-pass line 25 (by passing block fitting 2) and back into main flow line 20 either directly or through loop exit line 13 as shown. Check valve 26 prevents backflow into block fitting 2 through outlet 4.

Figure 4:
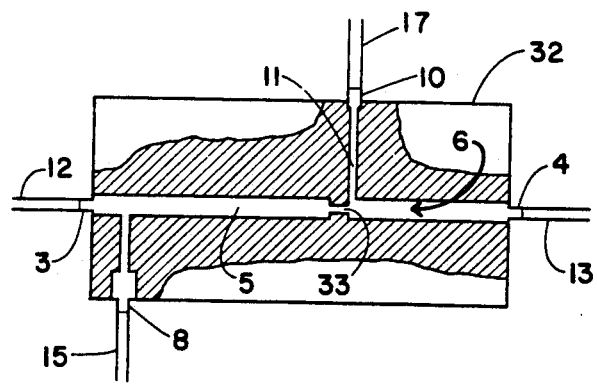
FIG. 4 is a side view of an alternate block fitting of the invention with portions removed to sectionally reveal the interior components of the fitting.

Samples are drawn from block fitting 2 utilizing the pressure differential created by pressure reducing means 6, positioned within interior passageway 5. It is preferable that pressure reducing means 6 take the form of venturi section 7 as shown. An alternate block fitting 32 is shown in FIG. 4, embodying an orifice 33 as pressure reducing means 6. As can be seen, by opening sample inlet valve 16 and sample exit valve 18, flow is established through sample passageway 9 in fitting 2, through sample port 8, sample inlet line 15, sample container 14, sample exit line 17, reentry port 10, reentry passageway 11, and into venturi section 7. In the embodiment shown in FIG. 4, reentry passageway 11 should enter interior passageway 5 just downstream of orifice 33. Valves 16 and 18 should remain open until flow is established, assuring a representative sample. Sample retention is accomplished by then closing valves 16 and 18. The sample container 14 (preferably a sample cylinder) may then be removed. Displaced gases and excess sample are thus returned to the main flow line by the system 1, resulting in little or no exposure of the sample to sampling personnel or the atmosphere.

The unique block fitting 2 (shown in partial section) is preferably unitary, and can be constructed by boring a block of material (preferably stainless steel) to form the various components described above. Thus the entire sampling process is performed by simply attaching the various lines, valves and block fitting 2 as shown to sample container 14 and main flow line 20. It should be here understood that the various lines shown may be of various lengths so as to accomplish sampling in particular locations. For example sample inlet line 15 may be very short, allowing a virtually direct connection between sample inlet valve 16 and sample port 8. Sample container 14 may then be oriented vertically with sample exit valve 18 on the top and block fitting 2 on the bottom to encourage purging of entrained gases from container 14. The rate of sampling may also be varied using valves 16, 18 and 21.

Figure 2:
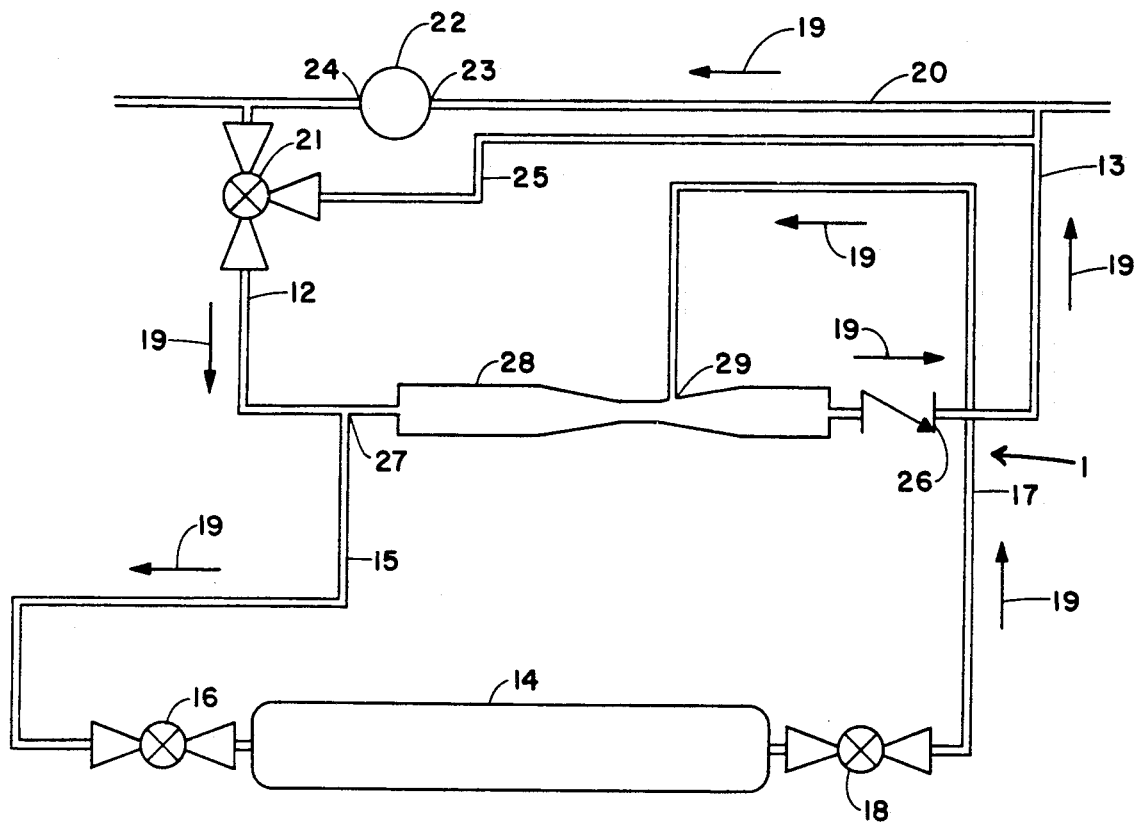
FIG. 2 is a side view of another embodiment of the invention utilizing standard fittings instead of the block fitting shown in FIG. 1.
Figure 3:
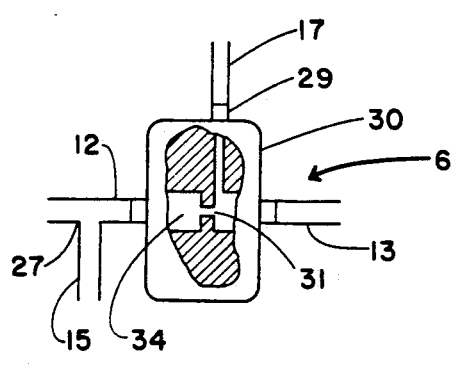
FIG. 3 is a side view of an alternate pressure reducing fitting of the invention with portions removed to sectionally reveal the interior components of the fitting.

FIG. 2 shows an alternate embodiment of the invention, wherein block fitting 2 is eliminated by inserting standard component fittings. As shown sample inlet line 15 is directly connected to loop entry line 12 by conventional means, such as tee connection 27. Just downstream from tee 27 is pressure reducing means 6, such as a venturi fitting 28 or an orifice fitting 30 (shown in FIG. 3), connected to loop entry line 12. Venturi fitting 28 (or orifice fitting 30) is provided with a reentry port 29, to which sample exit line 17 is attached. In the case of orifice fitting 30, reentry port 29 should extend to a point in orifice passageway 34 just downstream of the orifice 31. The utilization of component parts rather than block fitting (similar to those shown in FIG. 2) allows for custom configurations where space restrictions are a problem. It is preferable, however, that block fitting 2 be utilized wherever possible to maximize the strength and compactness of the system 1.

Figure 5:
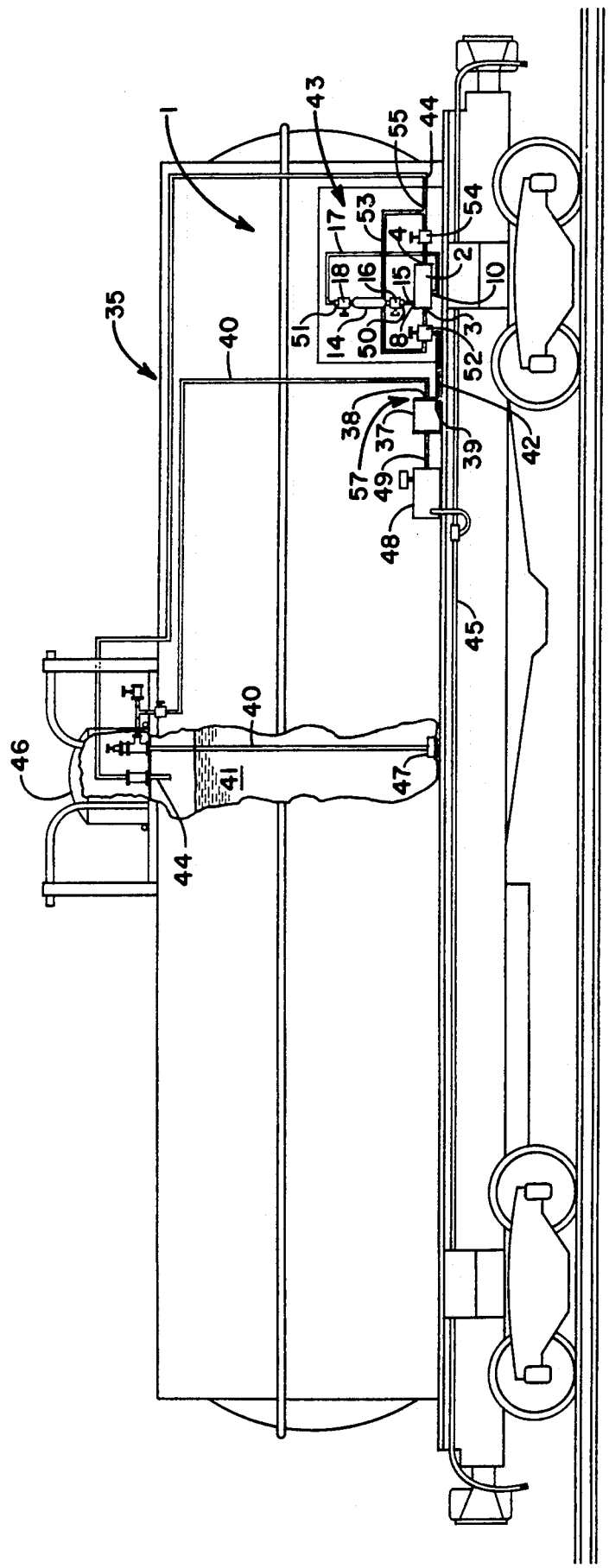
FIG. 5 is a side view of an embodiment of the invention in place on a railroad tank car.
Figure 6:
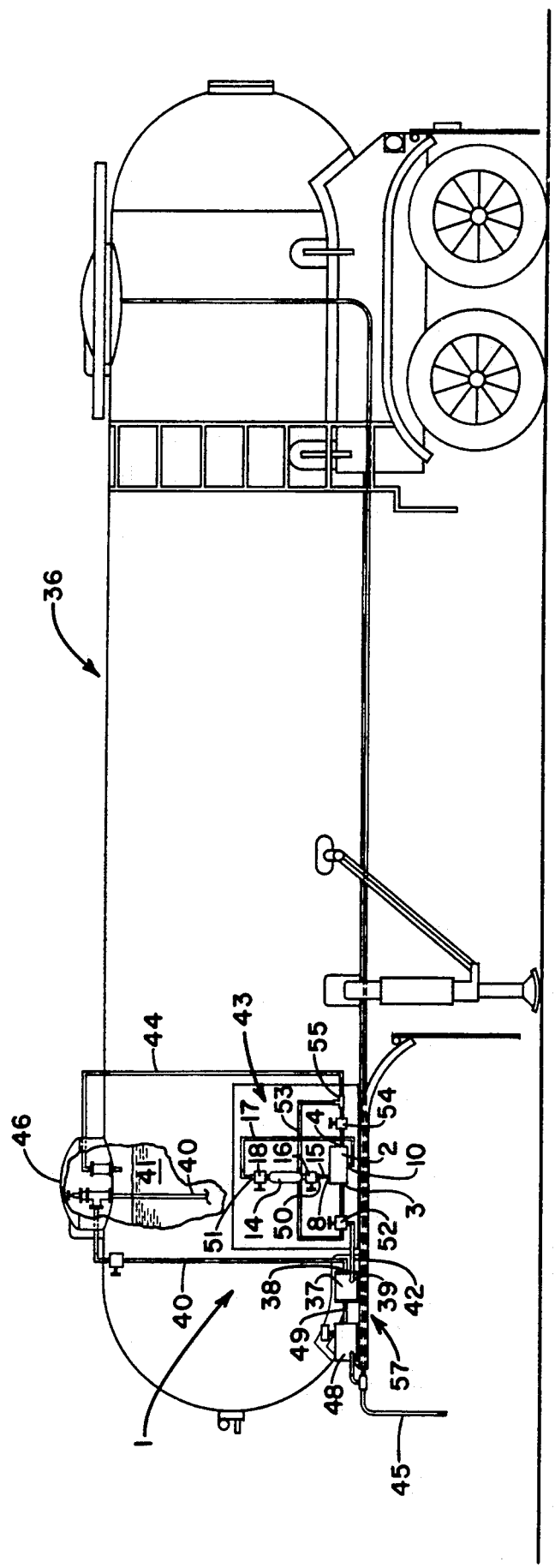
FIG. 6 is a side view of an embodiment of the invention in place on a highway tank trailer.
Figure 7:
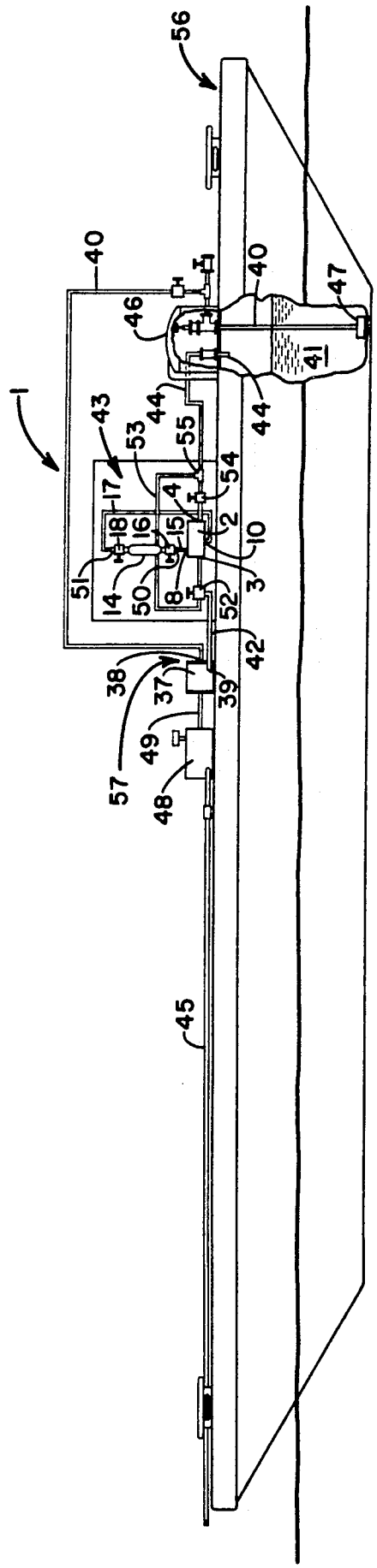
FIG. 7 is a side view of an embodiment of the invention in place on a marine barge.

A modified version of the system 1 may be used for closed loop sampling of fluids carried by wheeled transport tanks or marine transport tanks. For the purposes herein, the term "wheeled transport tanks" shall include railroad tank cars 35, such as the one shown in FIG. 5, and highway tank trailers 36, such as the one shown in FIG. 6. The term "marine transport tank" shall include marine-tankers or barges, such as the one shown in FIG. 7. Each wheeled transport tank 35, 36 or marine transport tank 56 includes a reservoir 41. As shown in FIGS. 5-7, the system 1 must additionally include a circulating means 57, such as a pump 37 having a suction port 38 and a discharge port 39, for circulating fluid from reservoir 41. When the fluid in reservoir 41 is a gas, circulating means 57 could take the form of a compressor (not shown). Suction line 40 runs from within reservoir 41 to suction port 38. Discharge line 42 runs from discharge port 39 to a sampling means 43. A return line 44 runs from sampling means 43 back to reservoir 41. A sample container 14 is removably connectable to sampling means 43.

As shown in FIGS. 5-7, access to the interior of reservoir 41 may be gained through existing hatches 46. Existing valves, piping and fittings on wheeled transport tank 35, 36 may form parts of suction line 40 and return line 44. It may be desirable to furnish a filter screen 47 at the end of suction line 40, as shown. Since pressurized gas lines 45 are usually available on wheeled transport tanks 35, 36, as well as some marine transport tanks 56, it is desirable that an air motor 48 be furnished to drive circulating means 57 via a coupling, such as a magnetic coupling 49. Sampling means 43 may include block fitting 2, sample inlet line 15, sample inlet valve 16, sample exit line 17 and sample exit valve 18, or other means known in the art, such as other versions of the invention 1 more particularly described herein. First and second double seal quick disconnect couplings 50, 51, such as Snap-Tite ™ H Series double seal quick disconnects, are provided to assure quick, leak-free changes of sample containers 14. A three-way valve 52 and a two-way valve 54 may be placed in discharge line 42 and return line 44, respectively coupled to a bypass line 53 (at three-way valve 54 and tee 55) for bypassing sample means 43 while homogeneous sample flow is established.

While it is preferable that all components of the system 1 be attached to transport tanks 35, 36, 56 this is not a necessity. For example, the entire sampling system 1 could be remotely mounted so as to couple to transport tanks 35, 36, 56 only when sampling is required. However, due to governmental body sampling requirements as well as other practical considerations, it is usually preferable that the system 1 be fixedly attached to transport tanks 35, 36, 56.

Operation of the system 1 shown in FIGS. 5-7 is simple. Air motor 48 is activated, establishing flow through the system 1. If desired, three-way valve 52 is opened between discharge line 42 and bypass line 53 and valve 54 is closed to cause initial flow to pass through bypass line 53 until a homogeneous, representative sample flow is established. Valve 52 is then opened between discharge line 42 and sampling means 43 and valve 54 is opened so as to allow flow to enter sampling means 43 and return through return line 44. Sampling means 43 is operated in the normal manner, depositing a sample in sample container 14. Sample container 14 is then removed and replaced with an empty container 14. Thus, prior art sampling methods for compressed gasses and liquids under pressure and resultant contamination of the atmosphere and exposure of sampling personnel or the wearing of bulky cumbersome safety equipment are eliminated.

As can be seen, the sample extraction system disclosed herein provides a safe and efficient means for sample extraction while preserving sample integrity. Many other embodiments of the invention will occur to those skilled in the art, and are intended to be included within the scope and spirit of the following claims.

I claim:

1. In combination with a wheeled transport tank having a reservoir, an improvement comprising a sample extraction system fixedly attached to said wheeled transport tank, including:
   a. a suction line extending into said reservoir;
   b. a circulating means, for circulating fluid from said reservoir, having a suction port and a discharge port; said suction port being connected to said discharge suction line;
   c. a discharge line having a first and a second end, connected at said first end to said discharge port;
   d. a block fitting, including:
      i. an inlet connected to said second end of said discharge line;
      ii. an outlet;
      iii. an interior passageway, providing communication between said inlet and said outlet thereby allowing fluid to flow through said block fitting;
      iv. a pressure reducing means, for causing a pressure drop within said interior passageway, positioned within said interior passageway;
      v. a sample port;
      vi. a sample passageway, connecting said interior passageway and said simple port between said inlet and said pressure reducing means;
      vii. a reentry port; and
      viii. a reentry passageway, connecting said reentry port and said pressure reducing means;
   e. a return line, connected on one end to said outlet of said block fitting and terminating within said reservoir;
   f. a sample container, having an inlet and an outlet;
   g. a sample inlet line, connected on one end to said sample port, and on the other end to said inlet of said sample container;
   h. a sample inlet valve, positioned in said sample inlet line;
   i. a sample exit line, connected on one end to said outlet of said sample container, ad on the other end to said reentry port; and
   j. at least one sample exit valve, positioned in said sample exit line; and
wherein said system defines a closed loop beginning and ending at said reservoir.

2. A sample extraction system according to claim 1, further comprising:
   k. a first double seal quick disconnect coupling, positioned in said sample inlet line between said sample inlet valve and said sample port; and
   l. a second double seal quick disconnect coupling, positioned in said sample exit line between said sample exit valve and said reentry port.

3. A sample extraction system according to claim 2, further comprising:
   m. an air motor, operatively connected to said circulating means.

4. A sample extraction system according to claim 1, further comprising:
   k. an air motor, operatively connect to said circulating means.

5. In combination with a marine transport tank having a reservoir, an improvement comprising a sample extraction system fixedly attached to said marine transport tank, including:
   a. a suction line extending into said reservoir;
   b. a circulating means, for circulating fluid from said reservoir, having a suction port and a discharge port, said suction port being connected to said suction line;
   c. a discharge line having a first end and a second end, connected at said first end to said discharge port;
   d. a block fitting, including:
      i. an inlet connected to said second end of said discharge line;
      ii. an outlet;
      iii. an interior passageway, providing communication between said inlet and said outlet thereby allowing fluid to flow through said block fitting;
      iv. a pressure reducing means, for causing a pressure drop within said interior passageway, positioned within said interior passageway;
      v. a sample port;
      vi. a sample passageway, connecting said interior passageway and said sample port between said inlet and said pressure reducing means;
      vii. a reentry port; and
      viii. a reentry passageway, connecting said reentry port and said pressure reducing means;

e. a return line, connected on one end to said outlet of said block fitting and terminating within said reservoir;
f. a sample container, having an inlet and an outlet;
g. a sample inlet line, connected on one end to said sample port, and on the other end to said inlet of said sample container;
h. a sample inlet valve, positioned in said sample inlet line;
i. a sample exit line, connected on one end to said outlet of said sample container, and on the other end to said reentry port; and
j. at least one sample exit valve, positioned in said sample exit line; and wherein said system defines a closed loop beginning and ending at said reservoir.

6. A sample extraction system according to claim 5, further comprising:
k. a first double seal quick disconnect coupling, positioned in said sample inlet line between said sample inlet valve and said sample port; and
l. a second double seal quick disconnect coupling, positioned in said sample exit line between said sample exit valve and said reentry port.

7. A sample extraction system according to claim 6, further comprising:
m. an air motor, operatively connected to said circulating means.

8. A sample extraction system according to claim 5, further comprising:
n. an air motor, operatively connected to said circulating means.

* * * * *